United States Patent [19]

Gewirtz

[11] Patent Number: 5,306,709
[45] Date of Patent: Apr. 26, 1994

[54] SUPPRESSION OF MEGAKARYOCYTOPOIESIS BY MACROPHAGE INFLAMMATORY PROTEINS

[75] Inventor: Alan M. Gewirtz, Philadelphia, Pa.

[73] Assignee: The University of Pennsylvania, Philadelphia, Pa.

[21] Appl. No.: 792,988

[22] Filed: Nov. 15, 1991

[51] Int. Cl.$^5$ .............................................. A61K 37/02
[52] U.S. Cl. .......................................... 514/12; 514/21
[58] Field of Search .................................... 514/12, 21

[56] References Cited

U.S. PATENT DOCUMENTS 4,493,795  1/1985  Nestor, Jr. et al. .................. 530/327
4,671,958  6/1987  Rodwell et al. ...................... 424/87

OTHER PUBLICATIONS

Broxmeyer et al., *Blood* vol. 76, No. 6 (Sep. 15, 1990) 1110-1116.
Graham et al., *Letters to Nature* vol. 344 (Mar. 1990).
Sherry et al., *J. Exp. Med.* 186, 2251-2259 (1988).
Zipfel et al., *J. Immunol.* 142, 1582-1590 (1989).
Irving et al., *Nucleic Acids Res.* 18, 3261-3270 (1990).
Wolpe et al., *Proc. Natl. Acad. Sci. USA* 86, 612-616 (1989).
Tekamp-Olson et al., *J. Exp. Med.* 172, 911-919 (1990).

Primary Examiner—Howard E. Schain
Assistant Examiner—Choon P. Koh
Attorney, Agent, or Firm—Seidel, Gonda, Lavorgna & Monaco

[57] ABSTRACT

Macrophage inflammatory protein-1 or -2, or analog thereof, is administered to a mammal to achieve therapeutic reduction of the number of circulating platelets. The proteins are useful in treating essential thrombocythemia and reactive thrombocytosis.

20 Claims, 1 Drawing Sheet

SUPPRESSION OF MEGAKARYOCYTOPOIESIS BY MACROPHAGE INFLAMMATORY PROTEINS

REFERENCE TO GOVERNMENT GRANT

The invention was made with government support under grant CA 36896 CA 01324 awarded by the National Institutes of Health. The government has certain rights in the invention.

FIELD OF THE INVENTION

The invention relates to the inhibition of megakaryocytopoiesis.

BACKGROUND OF THE INVENTION

Pluripotent hematopoietic stem cells are activated in the bone marrow to proliferate and differentiate into mature megakaryocytes, each of which is capable of releasing up to several thousand functional platelets in response to biological demand. Development of the stem cell proceeds by stages broadly corresponding to proliferation of progenitor cells, and differentiation of late progenitor and early precursor cells into mature megakaryocytes. Although regulation of this developmental process (megakaryocytopoiesis) is of substantial clinical interest for its potential application to disorders characterized by abnormal platelet production, endogenous factors responsible for stimulating or inhibiting proliferation and differentiation of megakaryocyte progenitor/precursor cells have not been thoroughly elaborated.

Thrombocytosis is a condition marked by the absolute increase in the number of circulating platelets. In some cases the elevation is acute and transient; in others it is chronic and persistent. The term "reactive thrombocytosis" has been commonly applied to define the concept that these patients have increased circulating platelet numbers in response to some underlying disease. This is in contrast to the condition where an autonomous drive to platelet production exists, commonly termed "thrombocythemia".

Reactive thrombocytosis may appear and persist as a result of chronic blood loss with iron deficiency, chronic inflammatory disease, chronic infectious disease, cancer and hemolytic anemia.

Primary thrombocythemia, also known as essential thrombocythemia, is an autonomous clonal proliferation of a pluripotent hematopoietic stem cell that results in an absolute increase in the number of circulating platelets. It shares several clinical features with other myeloproliferative disorders, most notably frequent bleeding and thrombotic lesions that represent major causes of morbidity and mortality.

Inhibitory factors capable of clinically significant megakaryocyte suppression have not been well-characterized. For example, both immunocytes and transforming growth factor-$\beta$ (TGF-$\beta$) have been studied as potential inhibitors of megakaryocytopoiesis, with inconclusive results (see, e.g., Blood 67, 479-483 and Blood 68, 619-626, (1986) Additionally, autoregulation via negative feedback mechanisms involving megakaryocyte products, including platelet-secreted 12-17kD glycoprotein, has been reported (J. Cell Physiol. 130, 361-368, (1987)). Platelet factor 4 and a synthetic C-terminal peptide have been shown to be capable of inhibiting megakaryocytopoiesis (Gewirtz et al., J. Clin Invest. 83, 1477-1486 (1989)). It has also been suggested that interferon-$\beta$ and interferon-$\gamma$ may have a role in regulating megakaryocyte colony formation (Ganser et al., Blood 70, 1173-1179 (1987); Chott et al., Br. J. Haematol. 74, 10-16 (1990)). While interferon-$\alpha$ has been used to lower platelet counts in patients with primary thrombocythemia and thrombocytosis associated with other types of malignant lesions, only approximately about 50% of patients achieve a stable state of remission. Moreover, on cessation of interferon therapy, recurrence of clinical and laboratory findings is usual (Gisslinger et al., Lancet 1, 634-637 (1989)).

While the potential utility of negative autocrine regulators or other megakaryocytopoiesis inhibitors in the clinical treatment of disorders characterized by excessively high platelet counts is apparent, none of the heretofore postulated inhibitors has so far proved useful in such applications.

Cytoreducive chemotherapeutic agents such as alkylating agents, radiophosporous and antimetabolites have been used to reduce platelet numbers. Most have leukemogenic potential. Their use has largely been abandoned in favor of hydroxyurea. However, hydroxyurea should at best be considered an agent with uncertain carcinogenic potential because at least one case of primary thrombocythemia conversion to acute leukemia has been linked to hydroxyurea therapy (Anker-Lugtenberg et al., Am. J. Hematol. 33:152 (1990)).

Anagrelide, a member of the imidazo (2, 1-b) quinazolin-2-one series, is an investigational drug which has been recently proposed for the treatment of thrombocytosis. Anagrelide has been shown to be capable of controlling platelet counts in most patients suffering from essential thrombocythemia as a consequence of an underlying myeloproliferative disorder. Suppression of platelet counts by anagralide appears to be selective relative to changes in white blood cell count and hemoglobin. However, the drug's potent effect on inhibiting platelet activation requires further study.

Macrophage inflammatory protein-1 (MIP-1) is a heparinbinding protein secreted by macrophages in response to lipopolysaccharide stimulation. MIP-1 is a major secretion product from stimulated macrophages, comprising about 2% of proteins secreted by endotoxin-stimulated cells. MIP-1 causes a local inflammatory response in mice and induces superoxide production in human neutrophils in vitro. It is also mildly chemokinetic for human neutrophils. MIP-1 is composed of two distinct peptides, MIP-1$\alpha$ and MIP-1$\beta$.

Macrophage inflammatory protein-2 (MIP-2), is another heparin-binding protein secreted by lipopolysaccharide-stimulated macrophages. It comprises about 0.5% of the proteins secreted by stimulated macrophages. Like MIP-1, MIP-2 has been shown to elicit a local inflammatory response when injected subcutaneously into mice. It has potent chemotactic activity for human polymorphonucleocytes. Also like MIP-1, MIP-2 is composed of two distinct peptides, MIP-2$\alpha$ and MIP-2$\beta$.

The activity of MIP-1 and MIP-2 in inhibiting megakaryocytopoiesis was unknown prior to the invention hereinafter described.

SUMMARY OF THE INVENTION

A method for suppressing megakaryocytopoiesis in a mammal is provided, which results in the reduction of the number of circulating platelets in the bloodstream of that mammal. An effective amount of macrophage inflammatory protein-1 (MIP-1), macrophage inflammatory protein-2, or analog of either, is administered to effect such platelet reduction. The invention is particularly useful in the treatment of disorders characterized by an excessively high platelet count. MIP suppresses megakaryocyte maturation (i.e., differentiation).

By "analog" with respect to MIP-1 or MIP-2 is meant a modified polypeptide having an amino acid sequence substantially the same as that of either MIP-1α or MIP-1β, or either MIP-2α or MIP-2β, respectively, in which one or more amino acids have been deleted or substituted, or in which one or more amino acids have been inserted; which modified polypeptide retains the property of inhibiting megakaryocytopoiesis.

DETAILED DESCRIPTION OF THE INVENTION

According to the invention, MIP-1α, -1β, -2α or -2β (collectively "MIP"), or analog thereof, is employed to inhibit megakaryocytopoiesis to effect in vivo reduction of platelet numbers. Sufficient MIP is given, preferably by intravenous administration, to decrease the number of circulating platelets. Depending upon the route of administration and idiosyncratic factors, most particularly the individual platelet count and the rate of MIP clearance, the average dosage may be as little as about 2.5 mg per day, up to several grams per day, for a human subject.

Figure 1:
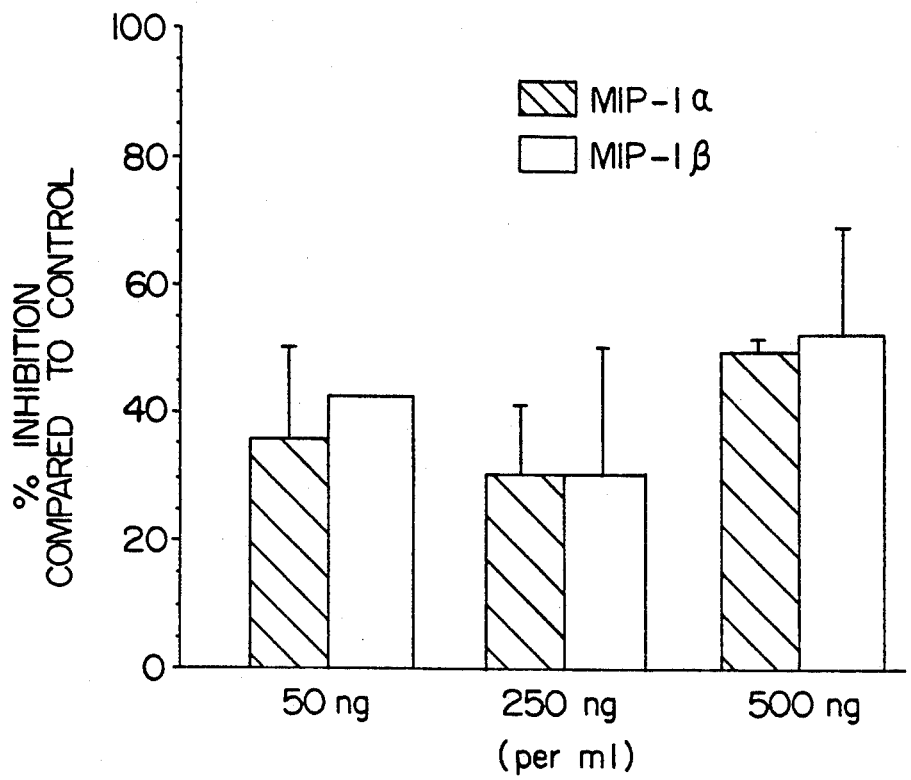
FIG. 1 is a graph of the effect of murine MIP-1α and MIP-1β on megakaryocyte colony formation at concentrations of 50, 250 and 500 ng/ml. The data are expressed as a percentage of inhibition compared to a control culture (no MIP).
Figure 2:
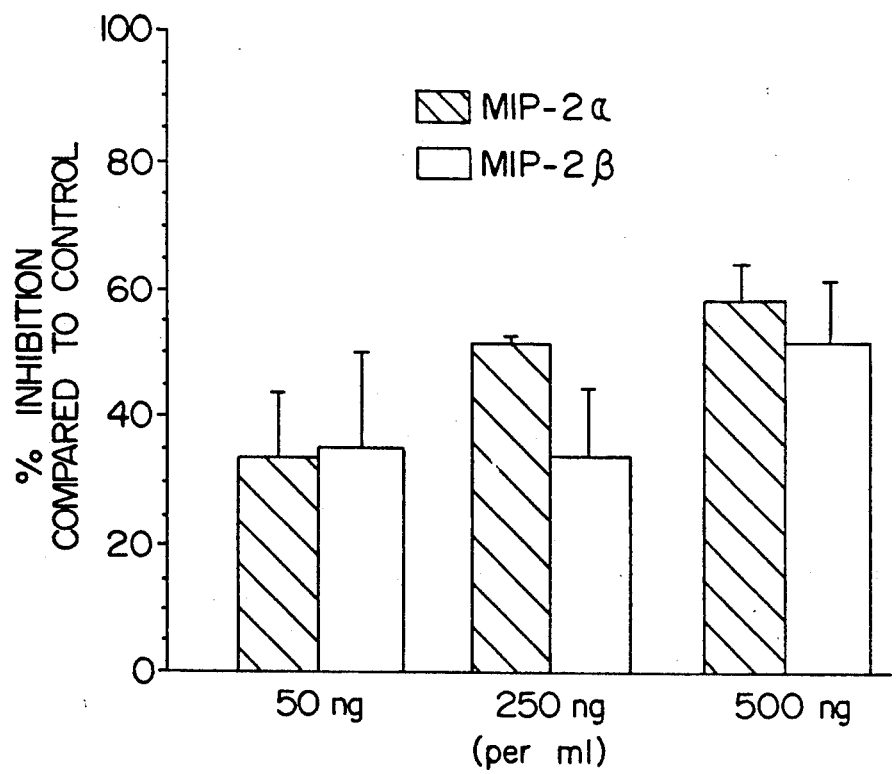
FIG. 2 is a graph of the effect of human MIP-2α and MIP-2β on megakaryocyte colony formation at concentrations of 50, 250 and 500 ng/ml. The data are again expressed as a percentage of inhibition compared to a control (no MIP).

Murine MIP-1α and MIP-1β have been isolated and cloned. See: Sherry et al., *J. Exp. Med.* 168, 2251-2259 (1988) (isolation of murine MIP-1 from endotoxin-stimulated RAW 264.7 cells (ATCC), followed by resolution of α and β types by SDS-hydroxylapatite chromatography, construction of a cDNA library and sequencing of the relevant cDNA). More recently, the genes coding for human MIP-1α and MIP-1β have been identified and the relevant cDNA and predicted amino acid sequences determined (Zipfel et al., *J. Immunol.* 142, 1582-1590 (1989); Irving et al., *Nucleic Acids Res.* 18, 3261-3270 (1990), both incorporated herein by reference). The human MIP-1α gene is designated "464" by Irving et al. The nucleotide sequence of the relevant cDNA and the predicted amino acid sequence are indicated in FIG. 1 thereof, and in FIG. 3 of Zipfel et al under the prior name "pAT 464" for the same gene. The cDNA and amino acid sequences for MIP-1α is also available from the EMBL/GenBank Data Library under accession number X52149.

The human MIP-1α gene has been designated "pAT 744" and 744.1" by the same investigators. The nucleotide sequence of the MIP-1β cDNA, and the predicted amino acid sequence, are indicated in FIG. 4 of Zipfel et al under the name pAT 744.

The amino acid sequences of human MIP-1α and MIP-1β are reproduced herein as SEQ ID NO:1 and SEQ ID NO:2, respectively.

Murine MIP-2 has previously been isolated and cloned. See: Wolpe et al., *Proc. Natl. Acad. Sci. USA* 86, 612-616 (1989) (isolation of murine MAP-2 from endotoxin-stimulated RAW 264.7 cells (ATCC)); Tekamp-Olson et al *J. Exp.Med.* 172, 911-919 (1990) (cloning of murine MIP-2). The latter investigators utilized a fragment of murine MIP-2 cDNA encoding most of the mature murine MIP-2 protein to probe a cDNA library prepared from poly(A)+RNA of the human monocytic-like cell line U937 (ATCC). The nucleotide sequence and predicted amino acid sequences of human MIP-2α and human MIP-2β have thus been reported (Id.) The cDNA and amino acid sequences are also available from the EMBL/GenBank Data Library under accession numbers X53799 (MIP-2α) and X53800 (MIP-2β). The disclosure of Tekamp-Olson et al. is incorporated herein by reference.

The amino acid sequences of human MIP-2α and MIP-2β are reproduced herein as SEQ ID NO:3 and SEQ ID NO:4, respectively.

MIP-1 and -2, and megakaryocytopoiesis-inhibiting analogs thereof, may be chemically synthesized by conventional solid phase synthetic techniques initially described by Merrifield, in *J. Am. Chem. Soc.* 15, 2149-2154 (1963). Other peptide synthesis techniques may be found, for example, in M. Bodanszky et al., *Peptide Synthesis*, John Wiley & Sons, 2d Ed. (1976) as well as in other reference works known to those skilled in the art. A summary of peptide synthesis techniques may be found in J. Stuart and J. D. Young, *Solid Phase Peptide Synthesis*, Pierce Chemical Company, Rockford, Ill. (1984). The synthesis of peptides by solution methods may also be used, as described in *The Proteins*, vol-II, 3d Ed., Neurath, H. et al., Eds., p. 105-237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973).

In general, these synthetic methods involve the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group, such as lysine.

Since the MIP amino acid sequences are known, the proteins may of course also be prepared by recombinant DNA techniques well-known to those skilled in the art. Moreover, analogs involving the substitution, deletion or insertion of one or more amino acids may similarly be prepared by such recombinant techniques, or by solid or liquid phase peptide syntheses, as described above.

It is contemplated, based upon the available MIP amino acid sequences, that MIP analogs may be prepared and effectively screened for ability to inhibit megarkaryocytopoiesis according to the megakaryocyte assay hereinafter described. In particular, it is contemplated that conservative amino acid changes may be made which do not alter the biological function of the peptide. For instance, one polar amino acid, such as glycine, may be substituted for another polar amino acid; or one acidic amino acid, such as aspartic acid may be substituted for another acidic amino acid, such as glutamic acid; or a basic amino acid, such as lysine, arginine or histidine may be substituted for another basic amino acid; or a non-polar amino acid, such as alanine, leucine or isoleucine may be substituted for another non-polar amino acid.

The degree of homology between the MIP analog and the corresponding native MIP amino acid sequence is preferably at least 80%, more preferably at least 90%, most preferably at least 95%.

MIP or MIP analogs are contemplated for use according to the invention in lowering blood levels of circulating platelets as deemed clinically advantageous, and for use in reducing the ability of these platelets to support blood clot formation. Pathological vascular reactions associated with excessively high platelet counts include stroke, pulmonary emboli, and related thromboembolic complications. A predisposing factor of these potentially fatal complications, high circulating platelet levels, may be substantially minimized by MIP. The invention is of particular clinical relevance in the treatment of myeloproliferative and other disorders characterized by clinically disadvantageous high platelet counts. Treatment of such disorders is accomplished according to the practice of the invention by the administration of MIP or MIP analog in sufficient quantities to suppress platelet production and approach normal hemostasis, as measured by significant reduction in platelet count of at least about 10%.

MIP or MIP analog may be administered by any convenient route which will result in the delivery to the bloodstream of a megakaryocytopoiesis-inhibiting effective amount. Contemplated routes of administration include parenteral and oral routes. Generally, the peptide may be administered in an amount sufficient to provide a blood plasma concentration of between about 10 and about 500 ng/ml, more preferably from about 20 to about 100 ng/ml. Plasma concentrations higher or lower than this may be utilized, depending on the nature of the treatment. Therapeutic dosages, based upon a 70 kg body weight, may range from about 0.1 mg to several grams per day. Preferably, the dosage ranges form about 0.1 to about 500 mg per day, most preferably from about 0.5 to about 50 mg per day.

For parenteral administration, MIP or an analog thereof may be given in any of the known pharmaceutical carriers useful for delivering polypeptide drugs. The carrier will typically comprise sterile water, although other ingredients to aid solubility or for preservation purposes may be included. Injectable suspensions may also be prepared in which appropriate liquid carriers, suspending agents, and the like may be employed. The parenteral routes of administration may comprise intravenous injection, intramuscular injection or subcutaneous injection, with intravenous injection being preferred.

For intravenous administration, the peptide may be dissolved in an appropriate intravenous delivery vehicle containing physiologically compatible substances such as NaCl, glycine and the like, having a buffered pH compatible with physiologic conditions. Such intravenous delivery vehicles are known to those skilled in the art.

MIP or an analog thereof may be operatively linked to a pharmaceutically acceptable carrier molecule to form a megakaryocytopoiesis-inhibiting complex. By "operatively linked" is meant any form of chemical or physical association or bond, including, but not limited to non-covalent complex formation, covalent bonding (including but not limited to covalent bonding by one or more cross-linking agents), and the like, which does not substantially interfere with the megakaryocytopoiesis-inhibiting activity of MIP.

Typically, the molecule carrier will comprise a protein, such as albumin, to improve the delivery of MIP and/or prolonging the half-life of MIP in the body. Techniques for protein conjugation through activated functional groups are particularly applicable. For a review of such techniques, see Aurameas et al., *Scan. J. Immunol,* 8, Supp. 1, 7-23 (1978). Also see U.S. Pat. Nos. 4,493,795 and 4,671,958. A wide range of homobifunctional and heterobifunctional cross-linking agents for covalently linking proteins are well known to those skilled in the art. For a partial list of such agents, see international patent application WO 90/14102 (1990), p. 29-31. Also included in the scope of such associations is the formation of a unitary protein by genetic engineering, resulting from the co-expression of genetic information for all or part of MIP and the carrier molecule as a single protein.

According to an exemplary treatment protocol, 12.5 mg of MIP or MIP analog of generally equivalent potency is administered intravenously to a 70 kg patient having distal ischemia, stroke, or other thromboembolic phenomena associated with abnormally elevated platelet count. The platelet count and function are monitored from seven to ten days after administration by analysis of blood samples taken at 4-hour intervals to evaluate MIP potency and clearance rates. At the end of the evaluation period, the dosage is adjusted as necessary to establish an improved platelet count or function, and the patient is again monitored once or twice weekly, as described. At the end of the period, the MIP dosage is again adjusted as necessary, with repetition of the described monitoring and evaluation procedure until the platelet count is substantially stabilized at a normal or near-normal level. The dosage required to obtain the desired stabilized platelet count comprises a therapeutic dosage according to the present invention. Indefinite daily administration of the therapeutic dosage may be necessary in order to maintain normal platelet levels during chronic thrombocytosis.

The practice of the invention is illustrated by the following non-limiting example.

EXAMPLE

The ability of the MIPs to inhibit megakaryocyte colony formation was demonstrated by the following assay.

Megakaryocyte colonies were cloned in plasma clot cultures as previously described (*Blood* 61, 384-9 (1983)). The cell population cultured consisted of either unseparated high density marrow mononuclear cells (MNC), or MNC depleted of adherent monocyte-macrophages and T lymphocytes using methods previously reported (*J. Immunol.* 139, 2915-2925 (1987)). To estimate basal growth conditions in marrow, the cultures contained no exogenous source of growth factors. To provide such essential growth factors, all cultures were supplemented with normal human AB serum (30% v/v) derived from the platelet-poor plasma of a single donor. Various amounts of pure recombinant murine MIP-1α and -1β, and pure recombinant MIP-2α and -2β, were added to the unseparated marrow MNC.

Megakaryocyte colonies were enumerated by indirect immunofluorescence assay utilizing a rabbit anti-human platelet glycoprotein antiserum as a megakaryocyte probe (ibid.). The antiserum used was highly specific for recognition of platelet glycoproteins. It does not recognize monocytes. A cluster of three or more intensely fluorescent cells was counted as one colony. The aggregate results of three such experiments are shown in FIG. 1 (MIP-1α and -1β) and FIG. (MIP-2α and -2β).

All four MIPs displayed an essentially equal ability to inhibit megakaryocyte colony formation in plasma clots, causing ~35% and ~50% inhibition at concentrations of 50 ng/ml and 500 ng/ml, respectively.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

I claim:

1. A method for reducing the number of circulating platelets in the bloodstream of a mammal comprising administering to the mammal an amount of macrophage inflammatory protein-1 and/or macrophage inflammatory protein-2 effective to inhibit megakaryocytopoiesis and thereby induce such a reduction.

2. A method according to claim 1 wherein the amount of macrophage inflammatory protein administered is sufficient to reduce the number of circulating platelets by at least about 10%.

3. A method according to claim 1 for treatment of thrombocytosis comprising administering to a human being a daily dosage of macrophage inflammatory protein of from about 0.1 to about 500 mg.

4. A method according to claim 3 wherein the daily dosage is from about 0.5 to about 50 mg.

5. A method according to claim 1 wherein the protein is macrophage inflammatory protein-1α.

6. A method according to claim 1 wherein the protein is macrophage inflammatory protein-1β.

7. A method according to claim 1 wherein the protein is macrophage inflammatory protein-2α.

8. A method according to claim 1 wherein the protein is macrophage inflammatory protein-2β.

9. A method for reducing the number of circulating platelets in the bloodstream of a mammal comprising administering to the mammal an amount of a macrophage inflammatory protein-1 analog or macrophage inflammatory protein-2 analog effective to inhibit megakaryocytopoiesis and thereby induce such a reduction.

10. A method according to claim 9 wherein the amount of macrophage inflammatory protein analog administered is sufficient to reduce the number of circulating platelets by at least about 10%.

11. A method according to claim 9 wherein the analog has at least 80% sequence homology any of human macrophage inflammatory proteins-1α, −2β, −2α or −2β.

12. A method according to claim 11 wherein the analog has at least 90% sequence homology with the human macrophage inflammatory protein.

13. A method according to claim 9 for treatment of thrombocytosis comprising administering to a human being a daily dosage of macrophage inflammatory protein analog of from about 0.1 to about 500 mg.

14. A method according to claim 13 wherein the daily dosage is from about 0.5 to about 50 mg.

15. A method for reducing the number of circulating platelets in the bloodstream of a mammal comprising administering to the mammal an amount of a conjugate effective to inhibit megakaryocytopoiesis and induce such a platelet number reduction, said conjugate comprising macrophage inflammatory protein-1, macrophage inflammatory protein-2, or analog of either macrophage inflammatory protein-1 or macrophage inflammatory protein-2, operatively linked to a pharmaceutically acceptable carrier molecule.

16. A method according to claim 15 wherein the carrier molecule comprises a protein.

17. A method according to claim 16 wherein the conjugate comprises a protein operatively linked to macrophage inflammatory protein-1α.

18. A method according to claim 16 wherein the conjugate comprises a protein operatively linked to macrophage inflammatory protein-1β.

19. A method according to claim 16 wherein the conjugate comprises a protein operatively linked to macrophage inflammatory protein-2α.

20. A method according to claim 16 wherein the conjugate comprises a protein operatively linked to macrophage inflammatory protein-2β.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 92 amino acids
( B ) TYPE: amino acid
( C ) STRANDEDNESS: single stranded
( D ) TOPOLOGY: linear ( x i ) SEQUENCE DESCRIPTION: SEQ ID NO:1:

```
Met Gln Val Ser Thr Ala Ala Leu Ala Val Leu Leu Cys Thr Met
                 5                  10                  15

Ala Leu Cys Asn Gln Phe Ser Ala Ser Leu Ala Ala Asp Thr Pro
                20                  25                  30

Thr Ala Cys Cys Phe Ser Tyr Thr Ser Arg Gln Ile Pro Gln Asn
                35                  40                  45

Phe Ile Ala Asp Tyr Phe Glu Thr Ser Ser Gln Cys Ser Lys Pro
                50                  55                  60

Gly Val Ile Phe Leu Thr Lys Arg Ser Arg Gln Val Cys Ala Asp
                65                  70                  75

Pro Ser Glu Glu Trp Val Gln Lys Tyr Val Ser Asp Leu Glu Leu
                80                  85                  90

Ser Ala
    92
```

( 2 ) INFORMATION FOR SEQ ID NO:2:

( i ) SEQUENCE CHARACTERISTICS:
( A ) LENGTH: 92 amino acids
( B ) TYPE: amino acid
( C ) STRANDEDNESS: single stranded
( D ) TOPOLOGY: linear ( x i ) SEQUENCE DESCRIPTION: SEQ ID NO:2:

```
Met Lys Leu Cys Val Thr Val Leu Ser Leu Leu Met Leu Val Ala
                 5                  10                  15

Ala Phe Cys Ser Leu Ala Leu Ser Ala Pro Met Gly Ser Asp Pro
                20                  25                  30

Pro Thr Ala Cys Cys Phe Ser Tyr Thr Ala Arg Lys Leu Pro Arg
                35                  40                  45

Asn Phe Val Val Asp Tyr Tyr Glu Thr Ser Ser Leu Cys Ser Gln
                50                  55                  60

Pro Ala Val Val Phe Gln Thr Lys Arg Ser Lys Gln Val Cys Ala
                65                  70                  75

Asp Pro Ser Glu Ser Trp Val Gln Glu Tyr Val Tyr Asp Leu Glu
                80                  85                  90

Leu Asn
    92
```

( 2 ) INFORMATION FOR SEQ ID NO:3:

( i ) SEQUENCE CHARACTERISTICS:
        ( A ) LENGTH: 73 amino acids
        ( B ) TYPE: amino acid
        ( C ) STRANDEDNESS: single stranded
        ( D ) TOPOLOGY: linear ( x i ) SEQUENCE DESCRIPTION: SEQ ID NO:3:

```
Ala Pro Leu Ala Thr Glu Leu Arg Cys Gln Cys Leu Gln Thr Leu
              5                  10                      15
Gln Gly Ile His Leu Lys Asn Ile Gln Ser Val Lys Val Lys Ser
             20                  25                      30
Pro Gly Pro His Cys Ala Gln Thr Glu Val Ile Ala Thr Leu Lys
             35                  40                      45
Asn Gly Gln Lys Ala Cys Leu Asn Pro Ala Ser Pro Met Val Lys
             50                  55                      60
Lys Ile Ile Glu Lys Met Leu Lys Asn Gly Lys Ser Asn
             65                  70          73
```

( 2 ) INFORMATION FOR SEQ ID NO:4:

( i ) SEQUENCE CHARACTERISTICS:
        ( A ) LENGTH: 73 amino acids
        ( B ) TYPE: amino acid
        ( C ) STRANDEDNESS: single stranded
        ( D ) TOPOLOGY: linear ( x i ) SEQUENCE DESCRIPTION: SEQ ID NO:4:

```
Ala Ser Val Val Thr Glu Leu Arg Cys Gln Cys Leu Gln Thr Leu
              5                  10                      15
Gln Gly Ile His Leu Lys Asn Ile Gln Ser Val Asn Val Arg Ser
             20                  25                      30
Pro Gly Pro His Cys Ala Gln Thr Glu Val Ile Ala Thr Leu Lys
             35                  40                      45
Asn Gly Lys Lys Ala Cys Leu Asn Pro Ala Ser Pro Met Val Gln
             50                  55                      60
Lys Ile Ile Glu Lys Ile Leu Asn Lys Gly Ser Thr Asn
             65                  70          73
```